(12) United States Patent
Jönsson et al.

(10) Patent No.: US 8,113,060 B2
(45) Date of Patent: Feb. 14, 2012

(54) PRESSURE SENSING DEVICE AND USE OF THE SAME IN A CONNECTING STRUCTURE

(75) Inventors: Lennart Jönsson, Bjärred (SE); Olof Jansson, Vellinge (SE); Eddie Nilsson, Höör (SE)

(73) Assignee: Gambro Lundia AB, Lund (SE)

( * ) Notice: Subject to any disclaimer, the term of this patent is extended or adjusted under 35 U.S.C. 154(b) by 140 days.

(21) Appl. No.: 12/530,613

(22) PCT Filed: Apr. 25, 2008

(86) PCT No.: PCT/SE2008/050475
§ 371 (c)(1),
(2), (4) Date: Mar. 18, 2010

(87) PCT Pub. No.: WO2008/140395
PCT Pub. Date: Nov. 20, 2008

(65) Prior Publication Data
US 2010/0186518 A1    Jul. 29, 2010

Related U.S. Application Data

(60) Provisional application No. 60/938,223, filed on May 16, 2007.

(30) Foreign Application Priority Data

May 15, 2007    (SE) ...................................... 0701189

(51) Int. Cl.
*G01L 7/00*    (2006.01)
(52) U.S. Cl. ......................................................... 73/756
(58) Field of Classification Search .................... None
See application file for complete search history.

(56) References Cited

U.S. PATENT DOCUMENTS

| | | | | |
|---|---|---|---|---|
| 5,646,352 A * | 7/1997 | Joseph et al. | ................... | 73/756 |
| 5,753,820 A * | 5/1998 | Reed et al. | ...................... | 73/706 |
| 5,955,659 A * | 9/1999 | Gupta et al. | ................. | 73/54.01 |
| 6,164,313 A * | 12/2000 | Walters | ......................... | 137/218 |
| 6,171,253 B1* | 1/2001 | Bullister et al. | .............. | 600/486 |

(Continued)

FOREIGN PATENT DOCUMENTS

DE    26 16 133 B1    10/1977

(Continued)

*Primary Examiner* — Andre Allen
(74) *Attorney, Agent, or Firm* — Nixon & Vanderhye P.C.

(57) ABSTRACT

A pressure sensing device adapted for having a liquid flowing there through and for sensing the pressure of said liquid. The device has a casing being fluid-tightly divided into a first and a second chamber by a flexible, impermeable wall. The first chamber has a first opening for the liquid, said opening being placed at the lower part of the chamber, and a second opening for the liquid, said opening being placed at the top of the first chamber. The second chamber has a measuring port, which is connectable to a pressure transducer for bringing the second chamber into gas-tight communication with the pressure transducer. The device has a first orifice to permit the liquid to flow into and out of the device, the orifice being placed at the upper part of the device at a higher level than the second opening. A first channel is connecting the first orifice with the first opening. A second orifice permits the liquid to flow out of and into the device and is placed at the lower part of the device at a lower level than the first opening. A second channel connects the second opening with the second orifice.

17 Claims, 5 Drawing Sheets

U.S. PATENT DOCUMENTS

| | | |
|---|---|---|
| 6,398,955 B1 | 6/2002 | Fumiyama et al. |
| 6,510,741 B2 * | 1/2003 | Condrea et al. ............... 73/747 |
| 6,526,357 B1 | 2/2003 | Soussan et al. |
| 6,820,490 B2 | 11/2004 | Mittelstein et al. |
| 7,316,163 B2 * | 1/2008 | Grudzien ..................... 73/718 |
| 2002/0026837 A1 * | 3/2002 | Condrea et al. ............... 73/747 |

FOREIGN PATENT DOCUMENTS

| | | |
|---|---|---|
| EP | 1 213 034 A1 | 6/2002 |
| EP | 1 213 035 A1 | 6/2002 |
| GB | 2 208 714 A | 4/1989 |
| WO | WO 2005/044340 A1 | 5/2005 |

\* cited by examiner

PRESSURE SENSING DEVICE AND USE OF THE SAME IN A CONNECTING STRUCTURE

CROSS REFERENCE TO RELATED APPLICATION

This application is a National Phase application based on PCT/SE2008/050475 filed Apr. 25, 2008, which claims the priority of Swedish Patent Application No. 0701189-3, filed May 15, 2007, and claims the benefit of U.S. Provisional Application No. 60/938,223, filed May 16, 2007, the content of all of which is incorporated herein by reference.

TECHNICAL FIELD

The present invention relates to a pressure sensing device. More particular it relates to a pressure sensing device adapted for having a liquid flowing there through and for sensing the pressure of said liquid. Said device having a casing being fluid-tightly divided into a first and a second chamber by a flexible, impermeable wall, said first chamber having a first opening for the liquid, said opening being placed at the lower part of the chamber, said first chamber having a second opening for the liquid, said opening being placed at the upper part of the chamber, said second chamber having a measuring port, which is connectable to a pressure transducer for bringing the second chamber into gas-tight communication with the pressure transducer.

Use of such a pressure sensing device in a connecting structure for an extracorporeal blood treatment machine is also included.

BACKGROUND OF THE INVENTION

There are a number of various extracorporeal blood treatments, such as hemodialysis, hemofiltration, hemodiafiltration and plasmapheresis. They all make use of a filter and are often called dialysis. A conventional filter comprises a first and a second compartment separated by a membrane, the first compartment having an inlet and an outlet for the circulation of blood there through and the second compartment having an outlet for draining a liquid (e.g. plasma water, plasma, used dialysis liquid). In case the treatment (e.g. hemodialysis) requires the circulation of a treatment liquid (e.g. a dialysis liquid) the second compartment also has an inlet.

In the above treatments, blood is withdrawn from the patient, flown through the first compartment of the filter, and returned to the patient. This part is the so called extracorporeal circuit. In hemodialysis, a dialysis liquid is simultaneously flown through the second compartment of the filter and the metabolic wastes contained in the blood migrate by diffusion through the membrane into the second compartment. In hemofiltration, a pressure difference is created across the membrane so that plasma water flows through the membrane into the second compartment. Metabolic wastes migrate by convection into the second compartment. In order to compensate for the loss of body fluid, the patient is simultaneously infused with a sterile substitution solution. Hemodiafiltration is a combination of hemodialysis and hemofiltration. In this treatment a dialysis liquid is flown through the second compartment and a substitution solution is infused into the patient. In plasmapheresis, a pressure difference is created across the membrane so that plasma (i.e. plasma water and proteins) flows through the membrane into the second compartment. Once treated, the plasma is returned to the patient.

A machine for performing any of the above treatments comprises a pump for withdrawing blood from the patient through a so called arterial line connected at one end to the vascular circuit of the patient and at the other end to the inlet of the first compartment of a filter. The blood is pumped through the filter and is returned to the patient via a so called venous line connected at one end to the outlet of the first compartment of the filter and at the other end to the vascular circuit of the patient. The treatment machine also usually comprises a first blood pressure sensor for measuring the pressure of blood in the arterial line upstream of the pump, a second blood pressure sensor for measuring the pressure of blood in the venous line, a bubble detector for detecting any air bubbles in the venous line and a clamp for closing the venous line, for example when an air bubble is detected by the bubble detector. Sometimes also a third blood pressure sensor is present for measuring the pressure of blood in the arterial line downstream of the pump.

As is known by the man skilled in the art it is important to thoroughly watch the patient and the system during the treatment, as e.g. by measuring the blood pressure at a number of different points in the system. It is also known that it may be fatal to the patient if air is introduced into his/her blood system. Air might have come into the system via unintentional leaks.

The lines used for each dialysis treatment are disposable, since they are flown through by body fluids, such as blood, and are regarded as contaminated. The pressure sensors used in this field are for the same reason often separated into two distinct parts, one blood side part and one transducer side part. The actual pressure transducer, which is often expensive, is then protected from direct contact with the blood and can thus be reused, while the part that has been in contact with the blood is disposable.

A pressure sensing device according to the above is known from WO 2005/044340. In this document it is also mentioned that a permanent blood-air interface causes blood clotting. In order to reduce the risk of blood clotting the extracorporeal circuit should be so designed as to reduce the blood-air interface.

A connecting structure for an extracorporeal blood treatment machine is also disclosed in WO 2005/044340.

DEFINITIONS

The terms higher level and lower level as used herein means in the vertical direction in relation to a horizontal plane.

SUMMARY OF THE INVENTION

One object of the present invention is to provide a pressure sensing device that decreases the blood-air interface. The pressure sensing device according to the invention is characterised in that the second opening for the liquid being placed at the top of the first chamber, a first orifice for the liquid into/out of the device being placed at the upper part of the device at a higher level than the second opening of the first chamber, a first channel is connecting the first orifice of the device with the first opening of the first chamber, a second orifice for the liquid out of/into the device being placed at the lower part of the device at a lower level than the first opening of the first chamber, a second channel is connecting the second opening of the first chamber with the second orifice of the device, wherein the highest level of the first chamber is at the same level as or at a higher level than the highest level of the second channel, a first duct is provided having a lower mouth and an upper mouth, said lower mouth being placed in the top of the first chamber and the upper mouth being placed in the first channel at a higher level than the lower mouth.

In an alternative embodiment the pressure sensing device according to the invention is characterised in that the second opening for the liquid being placed at the top of the first chamber, a first orifice for the liquid into/out of the device being placed at the upper part of the device at a higher level than the second opening of the first chamber, a first channel is connecting the first orifice of the device with the first opening of the first chamber, a second orifice for the liquid out of/into the device being placed at the lower part of the device at a lower level than the first opening of the first chamber, a second channel is connecting the second opening of the first chamber with the second orifice of the device, wherein the highest level of the second channel is at the same level as or at a higher level than the highest level of the first chamber, a first duct is provided having a lower mouth and an upper mouth, said lower mouth being placed in the top of the first chamber and the upper mouth being placed in the first channel at a higher level than the lower mouth, a tube is provided having a lower mouth and an upper mouth, said lower mouth being placed in the highest part of the second channel and the upper mouth being placed in the first channel at a higher level than the lower mouth.

The pressure sensing device according to the invention provides the advantage that if an air bubble has escaped through the pressure sensing device during a dialysis treatment it can easily be forced back through the pressure sensing device and out of the extracorporeal circuit. This will be described in more detail below.

Another object of the present invention is to enable use of such a pressure sensing device in a connecting structure for an extracorporeal blood treatment machine.

Further embodiments of the invention are also disclosed.

BRIEF DESCRIPTION OF THE DRAWINGS

FIGS. 7a and 7b are identical except that FIG. 7a shows the priming mode and FIG. 7b shows the treatment mode.

DETAILED DESCRIPTION OF THE INVENTION

Figure 8:
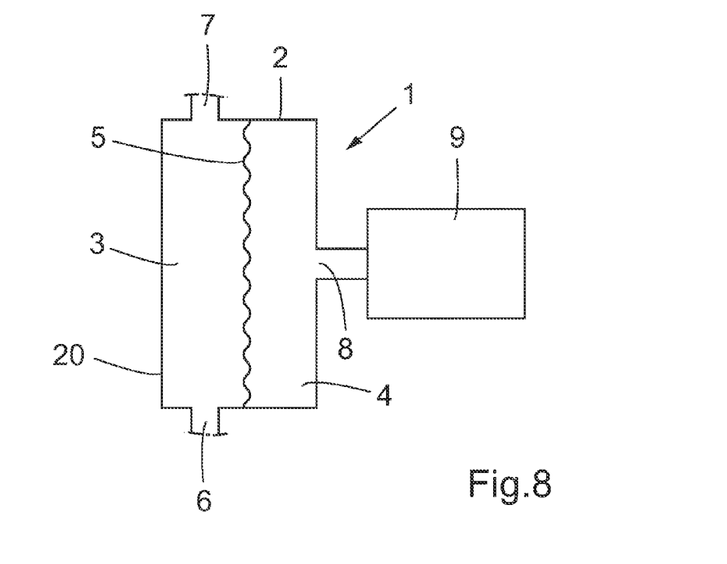
FIG. 8 shows schematically the basic principle of a pressure sensing device in cross section.

With reference to FIG. 8, the basic principle of a pressure sensing device 1 according to the prior art is shown schematically in cross section. A casing 2, which in the prior art is rigid and circular cylindrical is fluid-tightly divided into a first chamber 3 and a second chamber 4 by a circular, flexible, impermeable membrane 5. The second chamber 4 constitutes the transducer side part and has a measuring port 8 which is to be connected to an actual pressure transducer 9. The measuring port 8 is placed opposite the centre of the membrane 5. The pressure transducer 9 may be of any suitable type as is known in the art. The second chamber 4 in use contains a gas, in most cases air, and the connection to the pressure transducer 9 is gas-tight. The second chamber 4 does not come in contact with the blood or any other body fluid. The first chamber 3 is closed by the cylindrical casing 2, a side wall 20 of the cylindrical casing, and by the membrane 5 opposite the side wall 20. It is however adapted for a flow of blood there through and has an inlet 6 and an outlet 7 for the blood.

The pressure of the blood in the first chamber 3 acts on the membrane 5, which in turn acts on the gas in the second chamber 4. Since the second chamber 4 is a closed chamber, having contact only with the pressure transducer 9, the pressure of the gas in the second chamber 4 acts on the pressure transducer 9. Thus the pressure of the blood is sensed in the first chamber 3 and is transmitted via the membrane 5 and the gas in the second chamber 4 to the pressure transducer 9, which measures the pressure.

The above described principle is the same for the prior art and this invention, but some parts can differ, as will be described below.

According to the invention all external walls of the device 1 may of course be rigid as in the prior art. The function of the device may also be good with semi rigid external walls as long as they are more rigid than the membrane.

Figure 1:
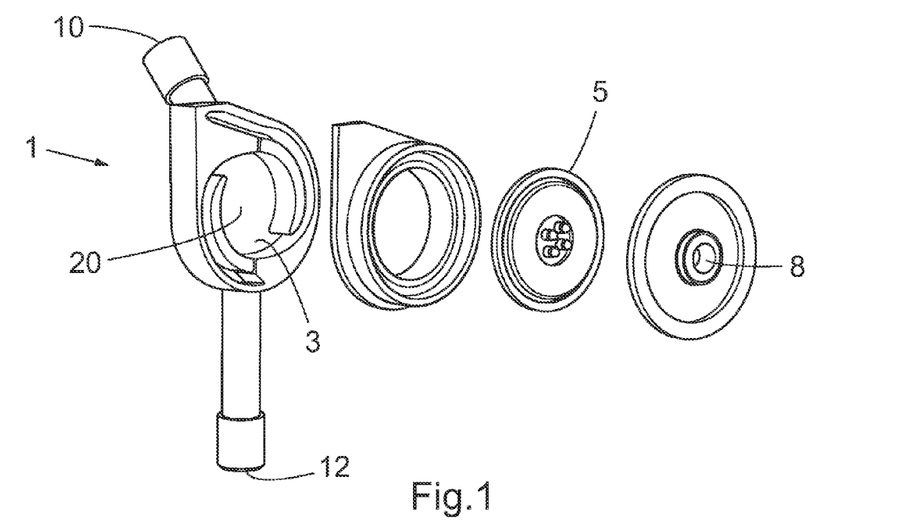
FIG. 1 is a front perspective exploded view showing one embodiment of the pressure sensing device according to the present invention.

With reference to FIG. 1 one embodiment of the pressure sensing device according to the present invention is shown. Also in this embodiment the membrane 5 is circular and when in place it covers the first chamber 3, which in this embodiment is circular cylindrical. The measuring port 8 placed opposite the centre of the membrane is also clearly shown. The form of the device 1 in this embodiment is generally flat with only a small extension in the direction perpendicular to the membrane and with the largest extension in parallel with the membrane.

Figure 2:
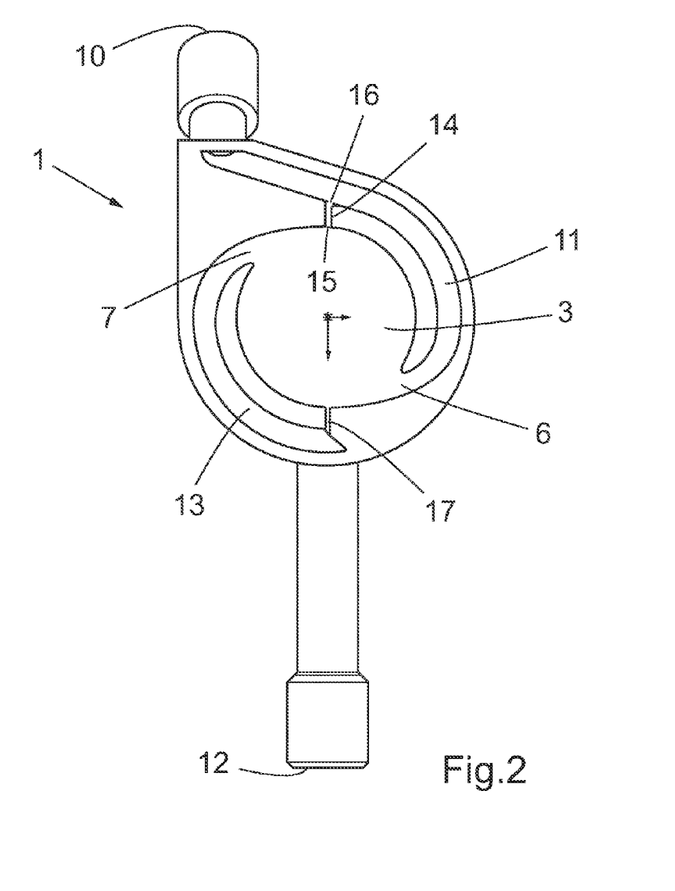
FIG. 2 is a front view of the embodiment in FIG. 1. The second chamber and the membrane have been lifted off to better show the interior of the device.

With reference to FIG. 2 the same embodiment as in FIG. 1 is shown, but the second chamber 4 and the membrane 5 have been lifted off to better show the interior of the device. As is described above with reference to FIG. 1, the form of the device 1 in this embodiment is generally flat in the direction perpendicular to the view shown in FIG. 2, except for the measuring port 8, extending in the direction perpendicular to the view shown in FIG. 2. I.e. the measuring port 8 extends horizontally and the geometrical length axis of the device extends in the vertical direction.

In the first description below, it is presumed that blood enters the first chamber 3 from below. However, the pressure sensing device according to the invention is in some applications intended to be flown through by e.g. blood or priming solution in the other direction. This will be explained in connection with FIG. 3.

The first opening 6 for the blood into the first chamber 3 is placed at the lower part of the chamber 3, and the second opening 7 for the blood out of the first chamber 3 is placed at the top of the chamber. As will be explained in further detail in connection with FIG. 3, it is beneficial for the decrease of the blood-air interface to fill the chamber 3 from below.

The device 1 has a first orifice 10 for the blood into the device. The first orifice 10 is placed at the upper part of the device at a higher level than the second opening 7 of the first chamber 3. The device also has a second orifice 12 for the blood out of the device. The second orifice 12 is placed at the lower part of the device at a lower level than the first opening 6 of the first chamber 3. In the embodiment shown in FIGS. 1 and 2, the second orifice 12 is placed on an axis right below the centre of the first chamber 3 at a distance from the first chamber 3. It may in an alternative embodiment be placed closer to the first chamber 3. The first orifice 10 is in the shown embodiment not in the same plane as the second orifice 12, but is placed in a tubing that is sloping backwards in relation to the device 1 and that is offset to the left in FIG. 2 in the plane of the device. In a preferred embodiment both the second orifice 12 and the first orifice 10 are placed on an axis right through the centre of the first chamber 3.

A first channel 11 connects the first orifice 10 of the device with the first opening 6 of the first chamber 3. A second channel 13 connects the second opening 7 of the first chamber 3 with the second orifice 12 of the device. Both channels 11, 13 make a smooth bend around the first chamber 3 outside the same as is shown in FIG. 2. It is a well known fact that sharp edges and corners and rough surfaces are to be avoided in parts flown through by blood to be as gentle as possible to the blood to avoid hemolysis. This implies that the channels 11, 13 are smoothly rounded also where the channel walls meet the side wall 20.

The embodiment of the invention shown in FIGS. 1 and 2 has a first duct 14, which has a lower mouth 15 and an upper mouth 16. Of course the lower mouth is always placed at a lower level than the upper mouth. The lower mouth 15 is placed in the top of the first chamber 3 and the upper mouth 16 is placed in the first channel 11 at a higher level than the lower mouth 15. The channels 11, 13 each have the same flow area as the respective lines that are to be connected to the first orifice 10 and to the second orifice 12. The first duct 14 has a smaller flow area than each of the channels 11, 13. Thus the main part of the flow goes through the first channel 11 and only a smaller part of the flow goes through the first duct 14. As an example the flow area of the duct 14 is 10% of the flow area of each of the channels.

Figure 3:
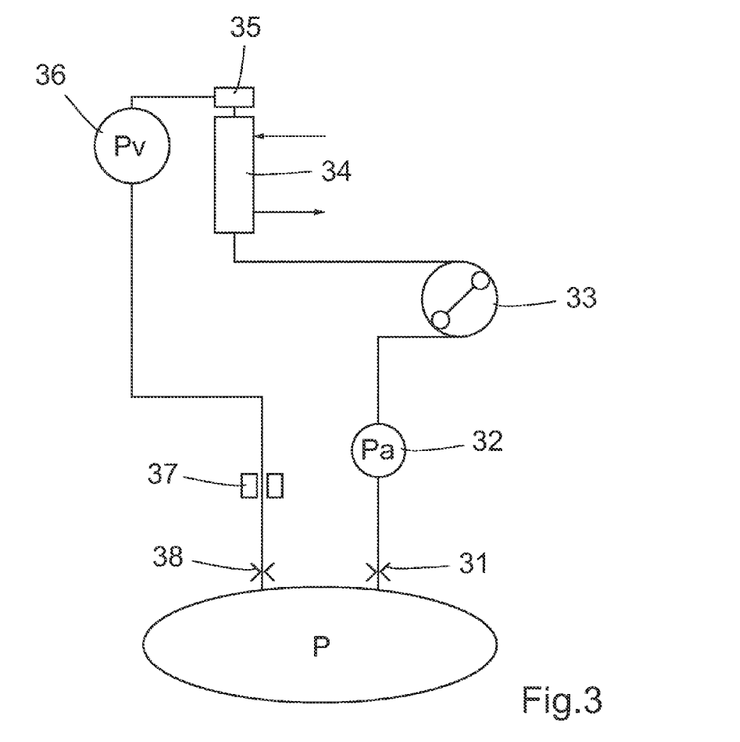
FIG. 3 shows schematically two pressure sensing devices according to the invention in a dialysis machine during treatment of a patient.

The function of the pressure sensing device according to the invention will now be described with reference to FIG. 3. In FIG. 3 a dialysis machine is schematically shown having pressure sensors 32, 36 with pressure sensing devices according to the invention used for measuring the pressures $P_a$ and $P_v$, i.e. the pressure in the arterial line and in the venous line, respectively. Starting from the patient P the blood is withdrawn from the patient P in the arterial line via a clamping means 31 and the pressure sensor 32 by a peristaltic pump 33 to the dialyzer 34. Downstream the dialyzer is a degassing device 35 for degassing the blood or for releasing any air bubbles in the blood before it is returned to the patient via the pressure sensor 36, a bubble detector 37 and a clamping means 38.

As is known in the art a priming is performed before a dialysis machine is connected to a patient. One object of the priming is to drive out the air from the system and fill it with a priming solution before it is connected to the patient. The dialysis machine shown in FIG. 3 is primed in the same direction as the blood is flowing during treatment. Thus, for priming, the arterial line is connected to a source of priming solution, not shown, and the venous line is connected to a drain, not shown. If the pressure sensor 36 for the pressure in the venous line has a pressure sensing device according to the embodiment shown in FIG. 2, the priming solution enters into the device via the first orifice 10, goes through the first channel 11 and into the first chamber 3 via the first opening 6. In doing this, the priming solution pushes the air in front of it into the first chamber 3. The first chamber 3 is filled with priming solution from below and as it fills, the air goes out via the second opening 7 into the second channel 13, out via the second orifice 12 and further down the venous line to the drain. When the level of the priming solution in the first chamber 3 reaches the second opening 7, the air has been forced out from the first chamber 3, and the priming solution also goes out via the second channel 13, the second orifice 12 and further down the venous line to the drain. The air has a tendency to rise in the first chamber 3 due to the fact that the chamber is wider than the channels 11, 13 and thus the flow rate is lower in the chamber than in the channels 11, 13. Since the flow rate is higher in the second channel 13, air in the second channel 13 is easier dragged along compared to in the first chamber 3. This makes it less likely that an air bubble will be left standing in the channel. When the priming has been completed the patient is connected to the dialysis machine, and as was mentioned above, the blood during treatment is pumped in the same direction as the priming was performed.

The dialysis machine shown in FIG. 3 is a system in which the blood-air interface is kept as small as possible. Thus, no new air is to come into the system once the priming has been started. If however, during treatment, an air bubble is detected by the bubble detector 37, a feedback signal is sent to make the machine stop the blood flow to the patient by temporarily activating the clamping means 38 to close the venous line and stopping the pump 33. Also the clamping means 31 is activated to close the arterial line. The air bubble is backed up through the pressure sensing device e.g. by using a syringe at the degassing device 35 for withdrawing blood and thereby the air bubble in the backwards direction. To enable movement of the air bubble the clamping means 38 have to be safely opened at a suitable point of time. In this use, all inlets of the pressure sensing device have become outlets and vice versa. The air bubble goes in via the second orifice 12, further up via the second channel 13, and out into the first chamber 3 via the second opening 7. In the first chamber 3, the air bubble strives upwards, and thus goes out via the lower mouth 15, which is placed in the top of the first chamber 3. The first duct 14, the main direction of which is upwards, leads the air bubble to the upper mouth 16, where it is discharged into the upper part of the first channel 11. From here the air bubble goes via the first orifice 10 to the degassing device 35. When the air bubble has been let out via the degassing device 35, the clamping means 31 may be deactivated and the pump 33 may be restarted in the treatment direction.

The priming of the pressure sensor 32 is done in the opposite direction compared to the pressure sensor 36. Thus, the priming solution enters into the device via the second orifice 12, goes through the second channel 13 and into the first chamber 3 via the second opening 7. The priming solution runs along the walls of the first chamber 3 down to the bottom of the chamber and rises up via the first opening 6 into the first channel 11 to the same height as in the chamber. Thus, also in this case the first chamber 3 is filled from below. The air goes out via the first channel 11 and via the duct 14, discharging into the upper part of the first channel 11, out through the first orifice 10. When the device is filled up to the level of the lower mouth 15, the last air is pressed out via the first duct 14 as the level rises into the duct and the device is completely filled up with priming solution to the first orifice 10. Thus the risk that an air bubble should be trapped within the pressure sensing device is substantially reduced.

Figure 4A:
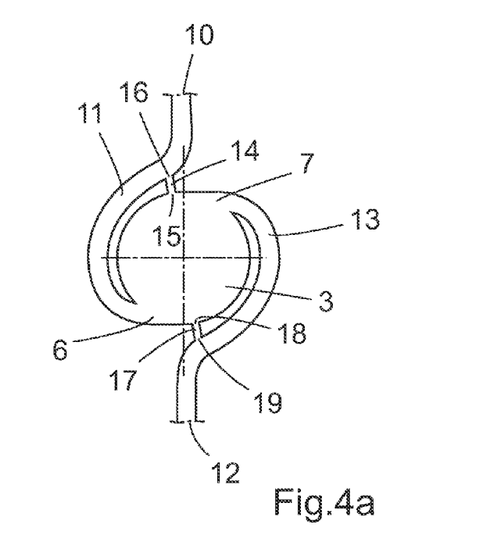
FIG. 4a shows schematically the principle of the embodiment in FIGS. 1 and 2.

FIG. 4a shows schematically the principle of the embodiment in FIG. 2. It is shown that the second opening 7 is placed at the top of the first chamber 3 and that the highest level of the first chamber 3 is at the same level as or at a higher level than the highest level of the second channel 13. With this construction the risk that an air bubble should be trapped in the channel is substantially reduced. In this particular embodiment the upper part of the channel 13 goes horizontally into the highest level of the first chamber 3 in its uppermost horizontal plane. It is however also possible for the channel 13 to have another slope into the first chamber 3 as long as the second opening 7 is placed at the top of the first chamber 3 and the highest level of the first chamber 3 is at the same level as or at a higher level than the highest level of the second channel 13. FIG. 4a also shows the first duct 14 and how the lower mouth 15 is placed in the top of the first chamber 3 and the upper mouth 16 placed in the first channel 11 at a higher level than the lower mouth 15. The first duct 14 is in one embodiment vertical and straight, but it is also possible for the duct to have another slope, as long as the lower mouth 15 is placed at a lower level than the upper mouth 16. The first duct 14 may also be bent. It is however better the steeper the slope of the first duct is and the straighter it is to ensure that the air or any air bubble is properly let out.

Due to the restricted space at the top of the first chamber 3, the second opening 7 and the lower mouth 15 must be spaced apart a very small distance. This distance shall be small enough not to allow trapping of an air bubble between the two, i.e. between the second opening 7 and the lower mouth 15.

As is shown in FIGS. 2 and 4a, the device 1 also has a second duct 17 having an upper mouth 18 and a lower mouth 19. The upper mouth 18 is placed in the lowest part of the first chamber 3 and the lower mouth 19 is placed in the second channel 13 at a lower level than the upper mouth 18. The purpose of the second duct 17 is to allow emptying of the chamber 3 when the treatment is finalized. It is important for dialysis patients not to loose more blood than necessary. Thus a rinse back is made to fill the system with a rinse back solution instead of the blood when the treatment is finalized. As for the example in FIG. 3 the arterial side is disconnected from the patient and the source for the rinse back solution is connected to the arterial side. The pumping direction is the same as during treatment giving the patient the blood in the system back via the venous line. When the rinse back solution reaches the first chamber 3 of the pressure sensor 36, the final blood residuals leave the chamber via the second opening 7, the second channel 13 and the second duct 17 and are thus given back to the patient. The second duct 17 has a smaller flow area than each of the channels 11, 13. As an example the flow area of the duct 17 is 10% of the flow area of each of the channels.

The second duct 17 is preferably vertical and straight, but it is also possible for the duct to have another slope, as long as the lower mouth 19 is placed at a lower level than the upper mouth 18. The second duct 17 may also be bent. It is however better the steeper the slope of the second duct is and the straighter it is to ensure that the liquid is properly let out.

Figure 4B:
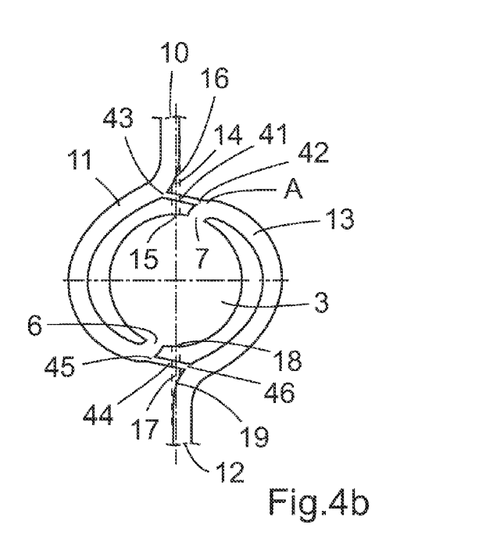
FIG. 4b shows schematically the principle of an alternative embodiment.

FIG. 4b shows schematically the principle of an alternative embodiment of the present invention. The second opening 7 is still placed at the top of the first chamber 3 but, counted from the second opening 7, the second channel 13 first reaches upwards so that its highest level A is at a higher level than the highest level of the chamber before it goes downwards. With this construction an air bubble could theoretically be trapped in the channel where it bends A. To avoid this, a tube 41 having a lower mouth 42 and an upper mouth 43 is placed between the bend A of the second channel 13 and the first channel 11. The lower mouth 42 is placed in the highest part A of the second channel 13 and the upper mouth 43 is placed in the first channel 11 at a higher level than the lower mouth 42.

The embodiment in FIG. 4b also has the first duct 14. Depending on the sizes of the first duct 14 and the tube 41, it may be preferred that the upper mouth 16 of the first duct 14 is placed at a higher level than the upper mouth 43 of the tube 41. The purpose is to ensure that air is not trapped but properly let out. If the upper mouth 16 of the first duct 14 is placed at a lower level than the upper mouth 43 of the tube 41, e.g. priming solution flowing with a high speed from the second channel 13 into the tube 41 could flow back into the upper mouth 16 of the first duct 14, and if the tube 41 is small, block the air passage out from the chamber 3.

The tube 41 is in one embodiment straight, but it may also be bent. It is however better the straighter it is to ensure that the air is properly let out. It is also better the steeper the slope of the tube is. The tube 41 has a smaller flow area than each of the channels 11, 13. Thus the main part of the flow passes through the first channel 11 and only a smaller part of the flow passes through the tube 41. As an example the flow area of the tube 41 is 10% of the flow area of each of the channels.

The duct and tube at the upper part of the pressure sensing device as in this embodiment may also be used if the highest level of the second channel 13 is at the same level as the highest level of the first chamber 3.

It is a particular advantage if the pressure sensing device is symmetrical in the sense that its upper right half is reversed and turned upside down in relation to its lower left half and its upper left half is reversed and turned upside down in relation to its lower right half.

It is however also possible to combine the upper half shown in FIG. 4a with the lower half shown in FIG. 4b and the upper half shown in FIG. 4b with the lower half shown in FIG. 4a.

In order to make the embodiment of FIG. 4b symmetrical in the sense described above, the first channel 11 makes a bend downwards before it goes upwards into the chamber 3. Thus, to allow emptying of this embodiment when the treatment is ready, the device has a conduit 44 having an upper mouth 45 and a lower mouth 46. The upper mouth 45 is placed in the lowest part of the first channel 11 and the lower mouth 46 is placed in the second channel 13 at a lower level than the upper mouth 45. The embodiment in FIG. 4b also has the second duct 17. Preferably, the lower mouth 19 of the second duct 17 is placed at a lower level than the lower mouth 46 of the conduit 44. The conduit 44 has a smaller flow area than each of the channels 11, 13. As an example the flow area of the conduit 44 is 10% of the flow area of each of the channels.

The conduit 44 is preferably straight, but it may also be bent. It is however better the steeper the slope of the conduit is and the straighter it is to ensure that the liquid is properly let out.

Figure 5:
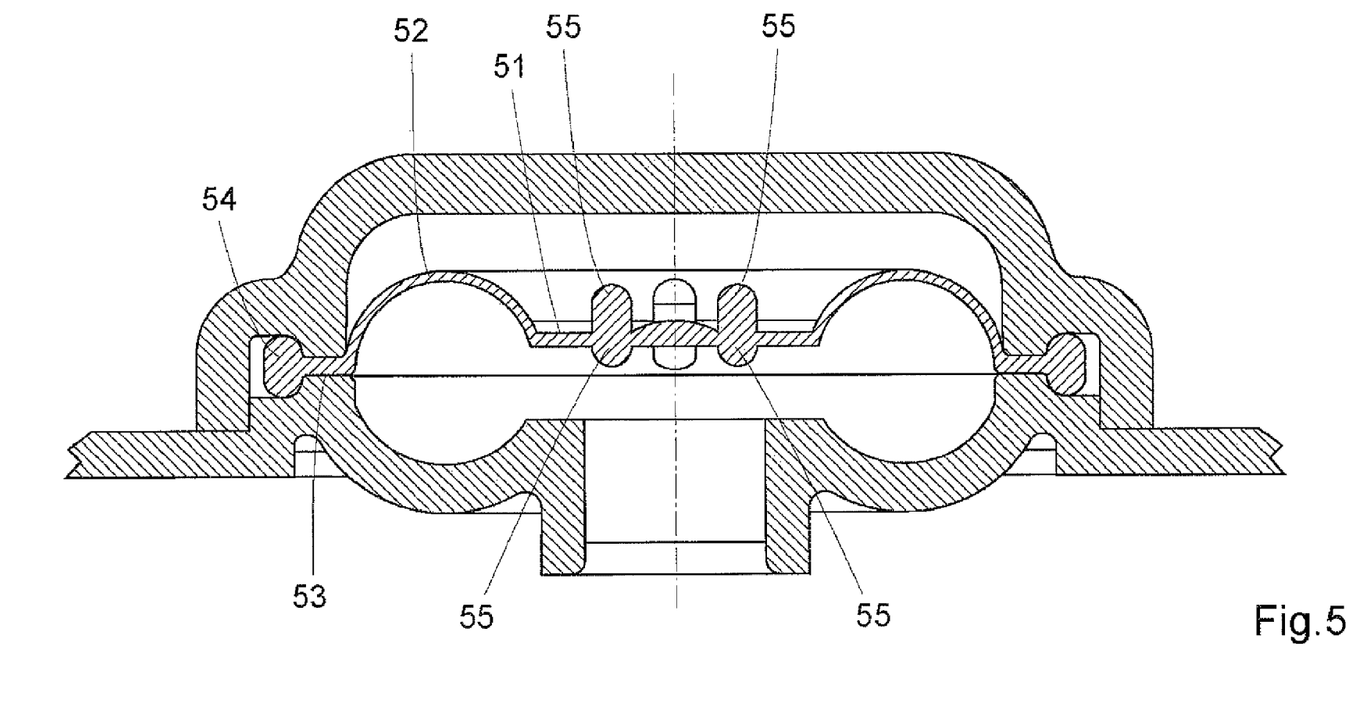
FIG. 5 is a sectional view through a pressure sensing device according to the prior art.

FIG. 5 is a sectional view through a pressure sensing device according to the prior art, especially showing the flexible, impermeable membrane. The same kind of membrane is preferably used in this invention. The membrane is circular having a central, flat, circular portion 51, connected to an annular portion 52 having a partly toroid surface, connected in turn to a narrow, peripheral, flat, annular portion 53, finally connected to a peripheral O-ring 54. The membrane has four projections 55 on each side from the central, flat, circular portion 51 to prevent blocking of the passage in the chambers 3, 4. The membrane 5 is turned with the convex side facing the first chamber 3 if the blood pressure is positive and with the convex side facing the second chamber 4 if the blood pressure is negative. The membrane must be non-toxic and must have appropriate flexibility properties. It may e.g. be made of silicone rubber or of Styrene-Ethylene/Butylene-Styrene. It is approved for contact with blood. It moves without stretch or friction, causing the pressure in the second chamber 4 to be equal to that in the first chamber 3.

The transfer of the pressure in the first chamber 3 to the second chamber 4 can be done by any flexible, impermeable wall causing the pressure in the second chamber 4 to be equal to that in the first chamber 3. In an alternative embodiment the wall 5 is a thin metal wall having flexible properties causing the pressure in the second chamber 4 to be equal to that in the first chamber 3. It is also possible to use a stiff plate with a flexible suspension to transfer the pressure in the first chamber 3 to the second chamber 4.

The pressure sensing device according to the invention in any of the above described embodiments is preferably one single unit (but not in one piece, since at least the membrane has to be in another material compared to the rest of the device). The pressure sensing device may be used in many types of dialysis machines, providing the advantage that it fills the chamber from below and decreases the blood-air interface.

Figure 6:
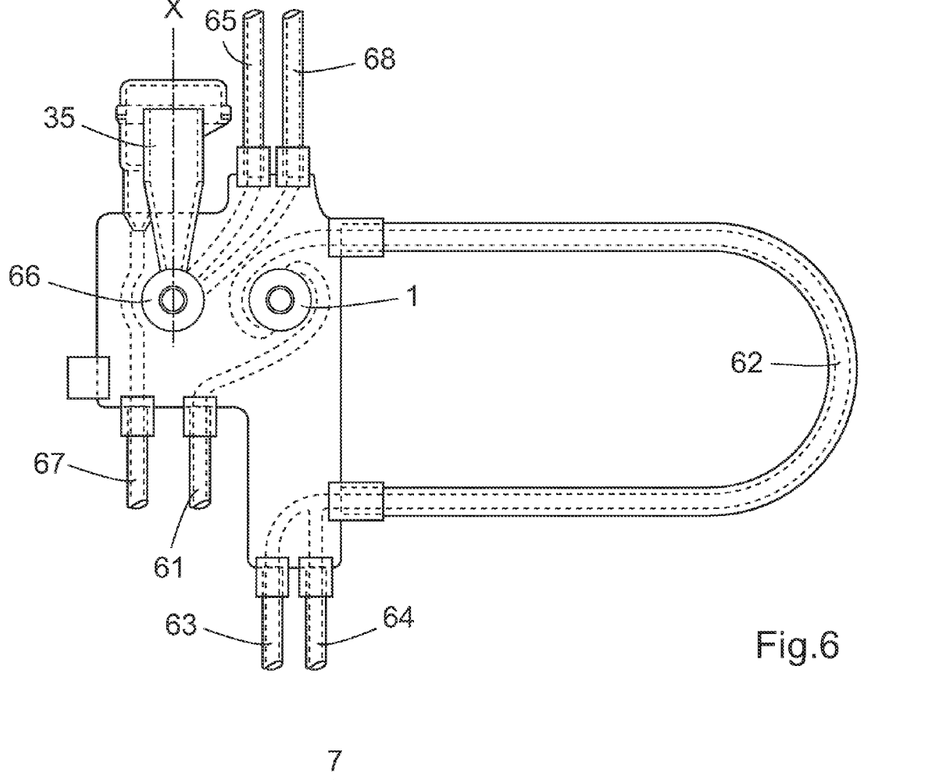
FIG. 6 shows the use of a pressure sensing device according to the invention in a connecting structure for an extracorporeal blood treatment machine.

FIG. 6 shows the use of a pressure sensing device according to the invention in a connecting structure for an extracorporeal blood treatment machine.

The connecting structure as such is known from WO 2005/044340, but one of the pressure sensing devices 1, the one to the right in FIG. 6 is of the type according to the present invention. A degassing device 35 is also shown. The document WO 2005/044340 discloses a number of embodiments of the connecting structure and all of the pressure sensing devices could be exchanged into pressure sensing devices according to the present invention.

In the connecting structure in FIG. 6 the blood comes in from the patient via an arterial line 61. The blood passes the pressure sensing device 1 and the pump (not shown), situated in the bending of a tubing 62. The blood is pumped to the dialyzer via a line 63. It is known in the art to add an anticoagulant to the blood during a dialysis treatment to prevent the blood from coagulating. If such an anticoagulant is needed it is injected via a line 64. The blood is returned from the dialyzer via a line 65. From here the blood is conducted via a pressure sensing device 66 to the degassing device 35, where it is degassed. Finally it is conducted back to the patient via a venous line 67. If a post dilution infusion is used, which may be done in e.g. hemofiltration, the infusion is made via a line 68.

Figure 7A:
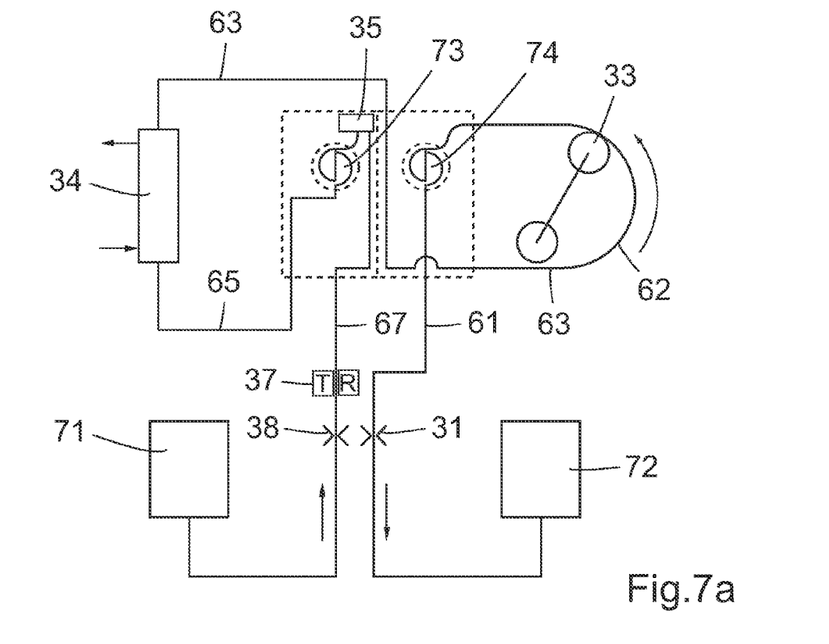
FIG. 7a shows the function of a connecting structure with pressure sensing devices according to the invention in a dialysis machine during priming before connection of a patient to the machine.

FIG. 7a shows the function of a connecting structure with pressure sensing devices according to the invention in a dialysis machine during priming before connection to a patient. Parts from FIGS. 3 and 6 are found also in FIGS. 7a and 7b and then have the same reference numbers as in FIGS. 3 and 6. Both pressure sensing devices in FIG. 7a are of the type according to the present invention. The pressure sensing device on the venous side has reference number 73 and the pressure sensing device on the arterial side has reference number 74. The system in FIG. 7a is as shown primed in the backwards direction i.e. from the venous side. Of course the whole system is primed, but in the following only parts of interest for this invention will be mentioned. The priming solution from the source 71 for the priming solution enters both the pressure sensing device 73 on the venous side and the pressure sensing device 74 on the arterial side via the first orifice 10, i.e. the priming is identical with what is described above in relation to priming of the pressure sensor 36 in FIG. 3. The priming solution is collected in a drain bag 72.

To avoid any problem caused by the pump sucking air via the degassing unit 35 instead of priming solution from the source 71, the source 71 for the priming solution should be placed at a level above the degassing unit 35. If the pump speed is also adjusted in accordance with the height of the source 71 for the priming solution above the degassing unit 35 the problems should be avoided.

Figure 7B:
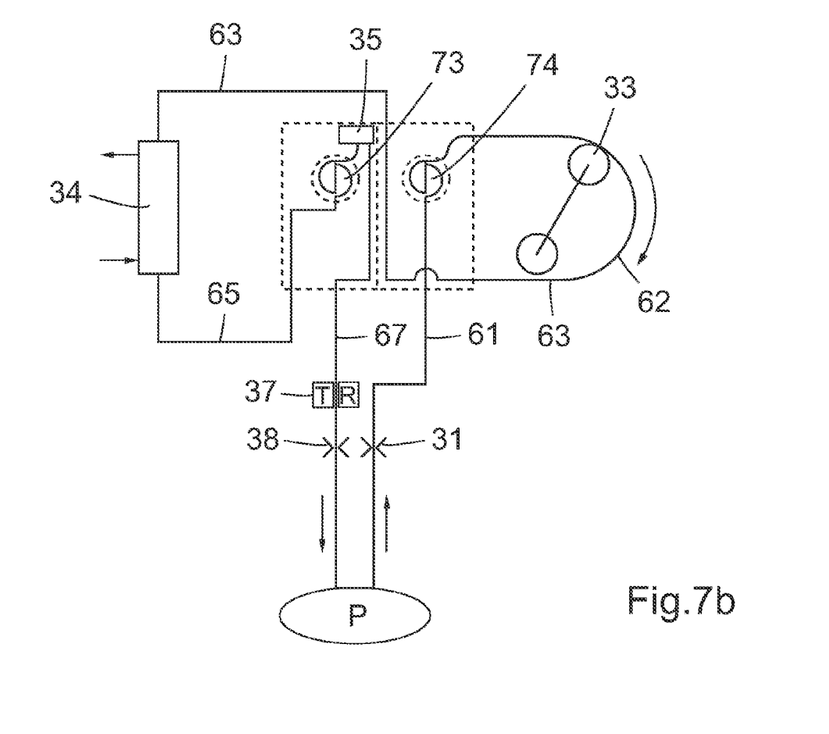
FIG. 7b shows the function of a connecting structure with pressure sensing devices according to the invention in a dialysis machine during treatment of a patient.

FIG. 7b shows the function of a connecting structure with pressure sensing devices according to the invention in a dialysis machine during treatment of a patient. FIGS. 7a and 7b are identical except for that FIG. 7a shows the priming mode and FIG. 7b shows the treatment mode. As shown, the flow direction of the blood during treatment is reversed compared to during priming. For both the pressure sensing devices 73, 74 this means that the blood enters via the second orifice 12 and goes out via the first orifice 10.

All embodiments described above for the pressure sensing device as a single unit may be used also in the connecting structure. The differences are described below.

The flow area of the first duct 14 in a pressure sensing device in a connecting structure may be bigger than what is mentioned above for a pressure sensing device as a single unit. The flow area of the first duct 14 is however still smaller than each of the channels 11, 13. Thus the main part of the flow still goes through the first channel 11 and only a smaller part of the flow goes through the first duct 14. As an example the flow area of the duct 14 is 10-40% of the flow area of each of the channels. As another example the flow area of the duct 14 is 10-25% of the flow area of each of the channels. As yet another example the flow area of the duct 14 is 10-15% of the flow area of each of the channels.

The same dimensions as for the first duct 14 are usable for the third duct 41.

If the second duct 17, and if needed also the fourth duct 44, are present they may be used for emptying rinse back solution from the chamber 3, or the first channel 11, which sometimes is a requirement for waste handling purposes. The majority of the blood has already been given back to the patient at the end of the treatment via the second opening 7 and the second channel 13.

Of course the pressure sensing device according to the invention may be used also in other types of connecting structures for extracorporeal blood treatment machines. The description in relation to FIGS. 6, 7a and 7b only gives an example of such use.

In the above the invention has been described as intended for pressure measurement in blood or another body fluid. The invention is however also suitable for pressure measurement in any liquid, especially where the actual pressure transducer is to be protected from the liquid. Examples of such cases are where the liquid is a strong acid or where hygiene regulations or risks of contamination require that the liquid is separated from the actual pressure transducer in that it is to be reused.

In the above the first and second chambers 3, 4 have been described as circular cylindrical. The cross section of the chambers could be altered into any other shape e.g. oval or squared, but to achieve a simple design it is an advantage if at least the wall 5 is kept circular. It is possible to have the wall circular and to vary the shape of the chambers both in a direction parallel and perpendicular to the wall.

It should be understood that various changes and modifications to the presently preferred embodiments described herein will be apparent to those skilled in the art. Such changes and modifications can be made without departing from the scope of the present invention and without diminishing its attendant advantages. It is therefore intended that such changes and modifications be covered by the appended claims.

The invention claimed is:

1. A pressure sensing device configured to permit a liquid to flow there through and to sense the pressure of said liquid, said device comprising:
   a casing being fluid-tightly divided into a first and a second chamber by a flexible, impermeable wall,
   said first chamber having a first opening for the liquid, said first opening being placed at the lower part of the chamber,
   said first chamber having a second opening for the liquid, said second opening being placed at the upper part of the chamber,
   said second chamber having a measuring port, connectable to a pressure transducer for bringing the second chamber into gas-tight communication with the pressure transducer, wherein the second opening for the liquid being is placed at the top of the first chamber,
   a first orifice for permitting the liquid to flow into and out of the device is placed at the upper part of the device at a higher level than the second opening of the first chamber, a first channel connects the first orifice of the device with the first opening of the first chamber,
   a second orifice for permitting the liquid to flow out of and into the device is placed at the lower part of the device at a lower level than the first opening of the first chamber, a second channel connects the second opening of the first chamber with the second orifice of the device, wherein the highest level of the first chamber is at the same level as or at a higher level than the highest level of the second channel, and
   a first duct is provided having a lower mouth and an upper mouth, said lower mouth being placed in the top of the first chamber and the upper mouth being placed in the first channel at a higher level than the lower mouth.

2. A pressure sensing device according to claim 1, wherein the first duct has a smaller flow area than the flow area of the first and second channels.

3. A pressure sensing device according to claim 2, wherein said first duct is configured in a vertical orientation.

4. A pressure sensing device according to claim 1, wherein the lowest part of the first chamber is at the same level as or at a lower level than the lowest part of the first channel and a second duct is provided having an upper mouth and a lower mouth, said upper mouth being placed in the lowest part of the first chamber and the lower mouth being placed in the second channel at a lower level than the upper mouth.

5. A pressure sensing device according to claim 1, wherein the lowest part of the first channel is at the same level as or at a lower level than the lowest part of the first chamber, a second duct is provided having an upper mouth and a lower mouth, said upper mouth being placed in the lowest part of the first chamber and the lower mouth being placed in the second channel at a lower level than the upper mouth, and conduit is provided having an upper mouth and a lower mouth, said upper mouth being placed in the lowest part of the first channel and the lower mouth being placed in the second channel at a lower level than the upper mouth.

6. A pressure sensing device according to claim 5, wherein the lower mouth of the conduit is placed at a higher level than the lower mouth of the second duct.

7. A pressure sensing device according to claim 1, wherein the device is one single unit.

8. A pressure sensing device configured to permit a liquid to flow there through and to sense the pressure of said liquid, said device having
   a casing being fluid-tightly divided into a first and a second chamber by a flexible, impermeable wall,
   said first chamber having a first opening for the liquid, said opening being placed at the lower part of the chamber,
   said first chamber having a second opening for the liquid, said opening being placed at the upper part of the chamber,
   said second chamber having a measuring port, which is connectable to a pressure transducer for bringing the second chamber into gas-tight communication with the pressure transducer, wherein the second opening for the liquid is placed at the top of the first chamber,
   a first orifice for permitting the liquid to flow into and out of the device being placed at the upper part of the device at a higher level than the second opening of the first chamber,
   a first channel connects the first orifice of the device with the first opening of the first chamber,
   a second orifice for permitting the liquid to flow out of and into the device being placed at the lower part of the device at a lower level than the first opening of the first chamber,
   a second channel connects the second opening of the first chamber with the second orifice of the device, wherein the highest level of the second channel is at the same level as or at a higher level than the highest level of the first chamber,
   a first duct is provided having a lower mouth and an upper mouth, said lower mouth being placed in the top of the first chamber and the upper mouth being placed in the first channel at a higher level than the lower mouth, and
   a tube is provided having a lower mouth and an upper mouth, said lower mouth being placed in the highest part of the second channel and the upper mouth being placed in the first channel at a higher level than the lower mouth.

9. A pressure sensing device according to claim 8, wherein the upper mouth of the tube is placed at a lower level than the upper mouth of the first duct.

10. A pressure sensing device according to claim 8, wherein the first duct and the tube have a smaller flow area than the flow area of the first and second channels.

11. A pressure sensing device according to claim 8, wherein said first duct is configured in a vertical orientation.

12. A pressure sensing device according to claim 8, wherein the lowest part of the first chamber is at the same level as or at a lower level than the lowest part of the first channel and a second duct is provided having an upper mouth and a lower mouth, said upper mouth being placed in the lowest part of the first chamber and the lower mouth being placed in the second channel at a lower level than the upper mouth.

13. A pressure sensing device according to claim 8, wherein the lowest part of the first channel is at the same level as or at a lower level than the lowest part of the first chamber, a second duct is provided having an upper mouth and a lower mouth, said upper mouth being placed in the lowest part of the first chamber and the lower mouth being placed in the second channel at a lower level than the upper mouth, and a conduit is provided having an upper mouth and a lower mouth, said upper mouth being placed in the lowest part of the first channel and the lower mouth being placed in the second channel at a lower level than the upper mouth.

14. A pressure sensing device according to claim 13, wherein the lower mouth of the conduit is placed at a higher level than the lower mouth of the second duct.

15. A pressure sensing device according to claim 8, wherein the device is one single unit.

16. Use of a pressure sensing device according to claim 1 in a connecting structure for an extracorporeal blood treatment machine.

17. A connecting structure for an extracorporeal blood treatment machine, wherein the connecting structure is provided with at least one pressure sensing device according to claim 1.

* * * * *